United States Patent [19]

Brandt

[11] Patent Number: 5,259,233
[45] Date of Patent: Nov. 9, 1993

[54] COUNTERFLOW VALVE

[75] Inventor: Michael D. Brandt, Chicago, Ill.

[73] Assignee: American Air Liquide, Countryside, Ill.

[21] Appl. No.: 690,627

[22] Filed: Apr. 24, 1991

[51] Int. Cl.$^5$ .......................................... F16K 11/056
[52] U.S. Cl. ................................... 73/1 G; 73/31.03; 137/597; 137/625.2; 137/625.43
[58] Field of Search .................. 73/31.03, 1 G, 864.83, 73/864.84; 137/625.43, 625.21, 597; 422/103, 62; 436/9

[56] References Cited

U.S. PATENT DOCUMENTS

| | | | |
|---|---|---|---|
| 1,344,490 | 6/1920 | Downie | 137/625.43 X |
| 3,021,713 | 2/1962 | Wright | 137/597 X |
| 3,038,449 | 6/1962 | Murphy, Jr. et al. | 137/597 X |
| 3,166,098 | 1/1965 | Jennings | 137/625.43 |
| 3,222,135 | 12/1965 | Ashmead | 137/597 X |
| 4,003,547 | 1/1977 | Snyder et al. | 251/31 |
| 4,114,419 | 9/1978 | Kimbell | 73/1 G |
| 4,127,167 | 11/1978 | Arendt | 166/85 |
| 4,218,884 | 8/1980 | Gold | 137/596 X |
| 4,285,195 | 8/1981 | Budzich | 137/596 X |
| 4,475,665 | 10/1984 | Norton | 222/14 |
| 4,476,094 | 10/1984 | Carson | 208/DIG. 1 X |
| 4,849,174 | 7/1989 | Brandt et al. | 422/62 |
| 4,891,186 | 1/1990 | Roberge et al. | 422/83 |
| 5,199,295 | 4/1993 | Mettes | 73/1 G |

FOREIGN PATENT DOCUMENTS 3421263 12/1985 Fed. Rep. of Germany .
236981 10/1986 Japan ................ 137/625.43

OTHER PUBLICATIONS

*Journal of Physics E. Scientific Instruments*, vol. 17, No. 4, Apr. 1984, pp. 263-264, Jones and Bott. "A Simple Fast Acting Gas Selection Valve".
Patent Abst. of Japan, vol. 11, No. 368 (M-647) 2 Dec. 1987 and JP-A-62 141 400 24 Jun. 1987.
Patent Abst. of Japan, vol. 11, No. 326 (C-454) 23 Oct. 1987 and JP-A-62 110 737 21 May 1987.
Patent Abst. of Japan, vol. 14, No. 159 (M-967) 28 Mar. 1990 and JP-A-2 021 077 24 Jan. 1990.
Patent Abst. of Japan, vol. 13, No. 336 (C-623) 27 Jul. 1989 and JP-A-1 115 806 9 May 1989.

*Primary Examiner*—Tom Noland
*Attorney, Agent, or Firm*—Oblon, Spivak, McClelland, Maier & Neustadt

[57] ABSTRACT

A counterflow valve for switching between flowing gas streams without undesirable interaction of the gas with any dead volume area or non-metallic surfaces or both, which valve contains a four-way double ported ball valve having a first and second input and a first and second output, first and second inlet duct, a back pressure regulator, adjustable flow control orifice and a valve outlet duct.

7 Claims, 6 Drawing Sheets

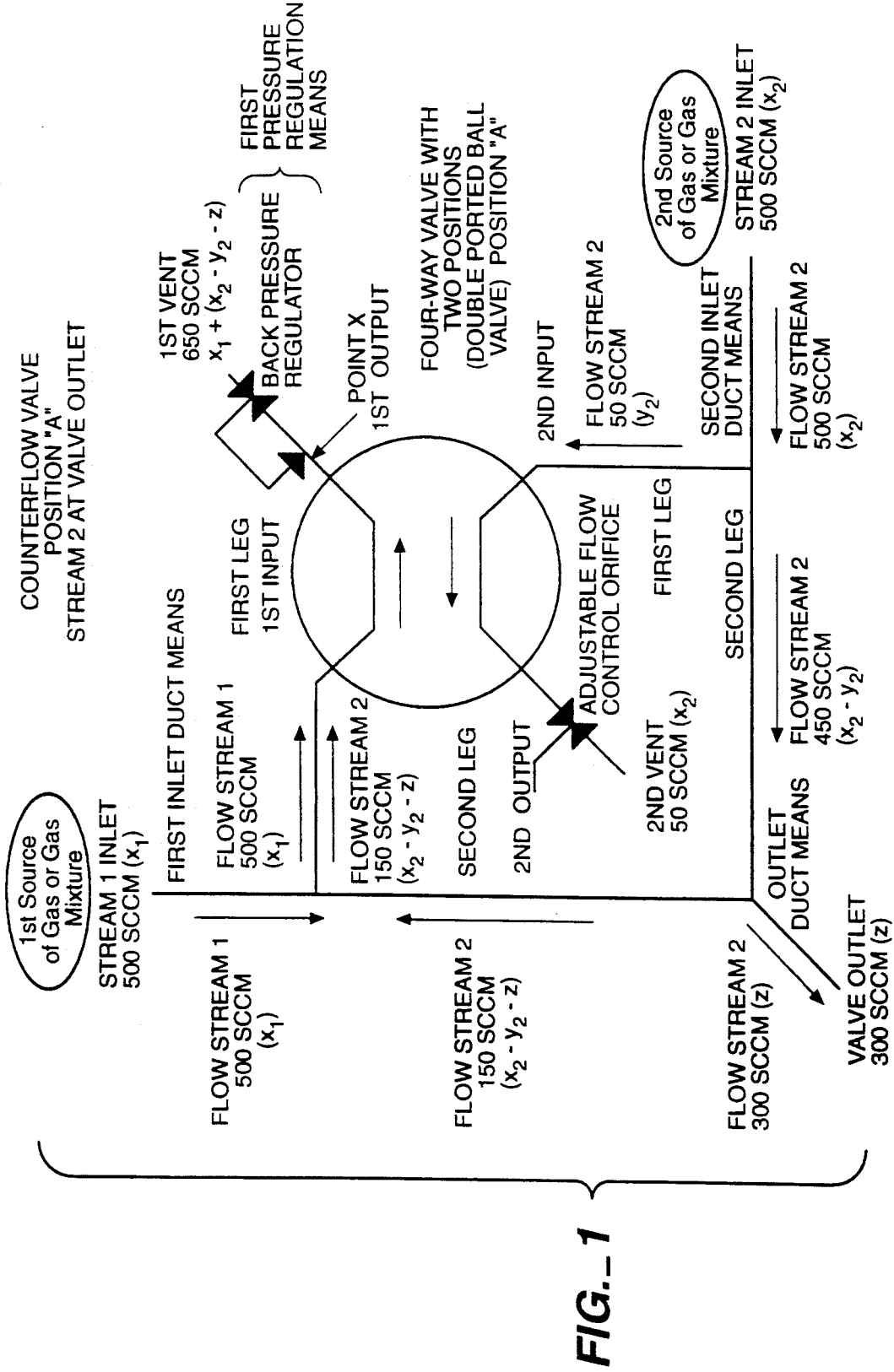
FIG._1

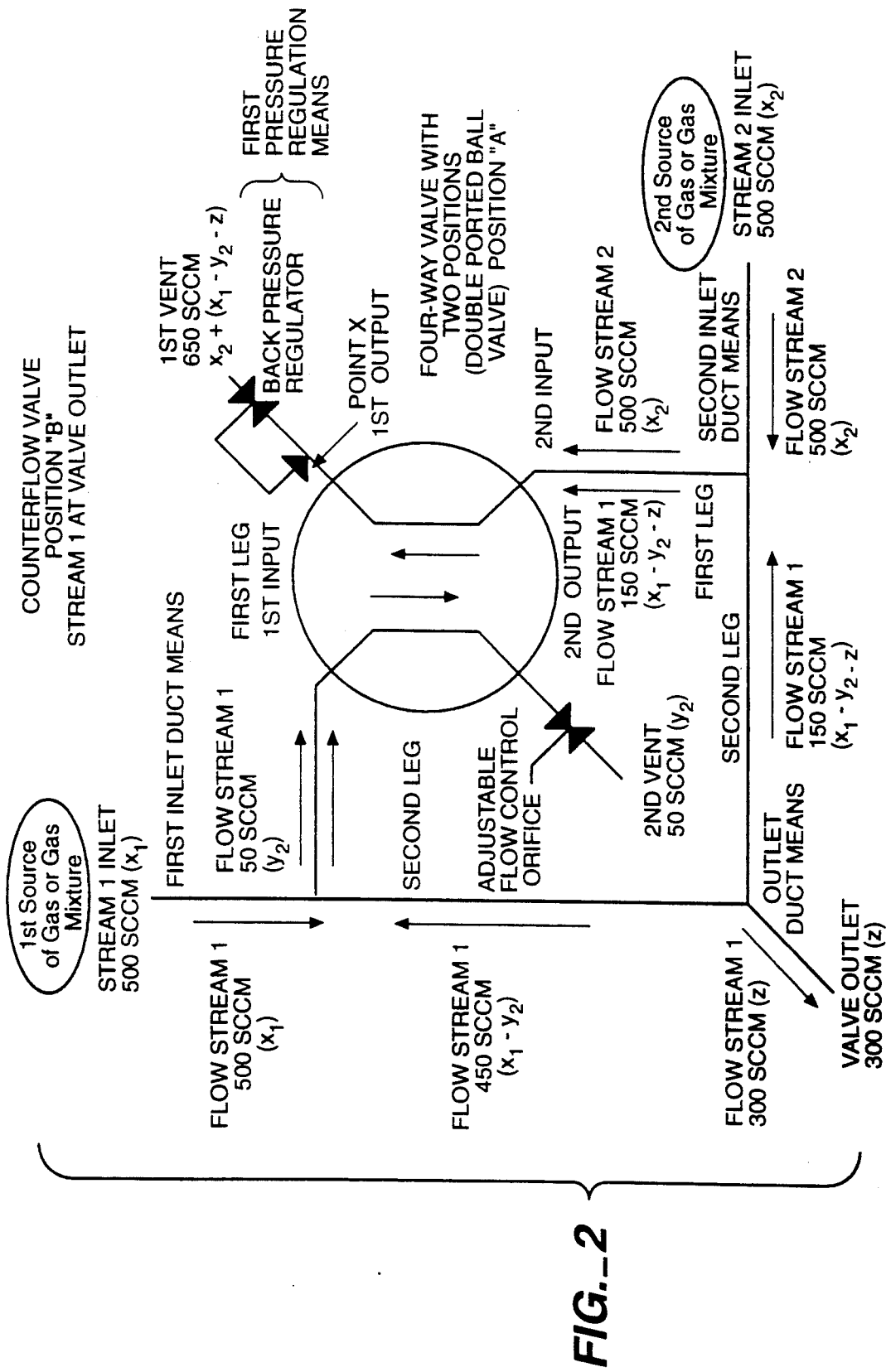
FIG._2

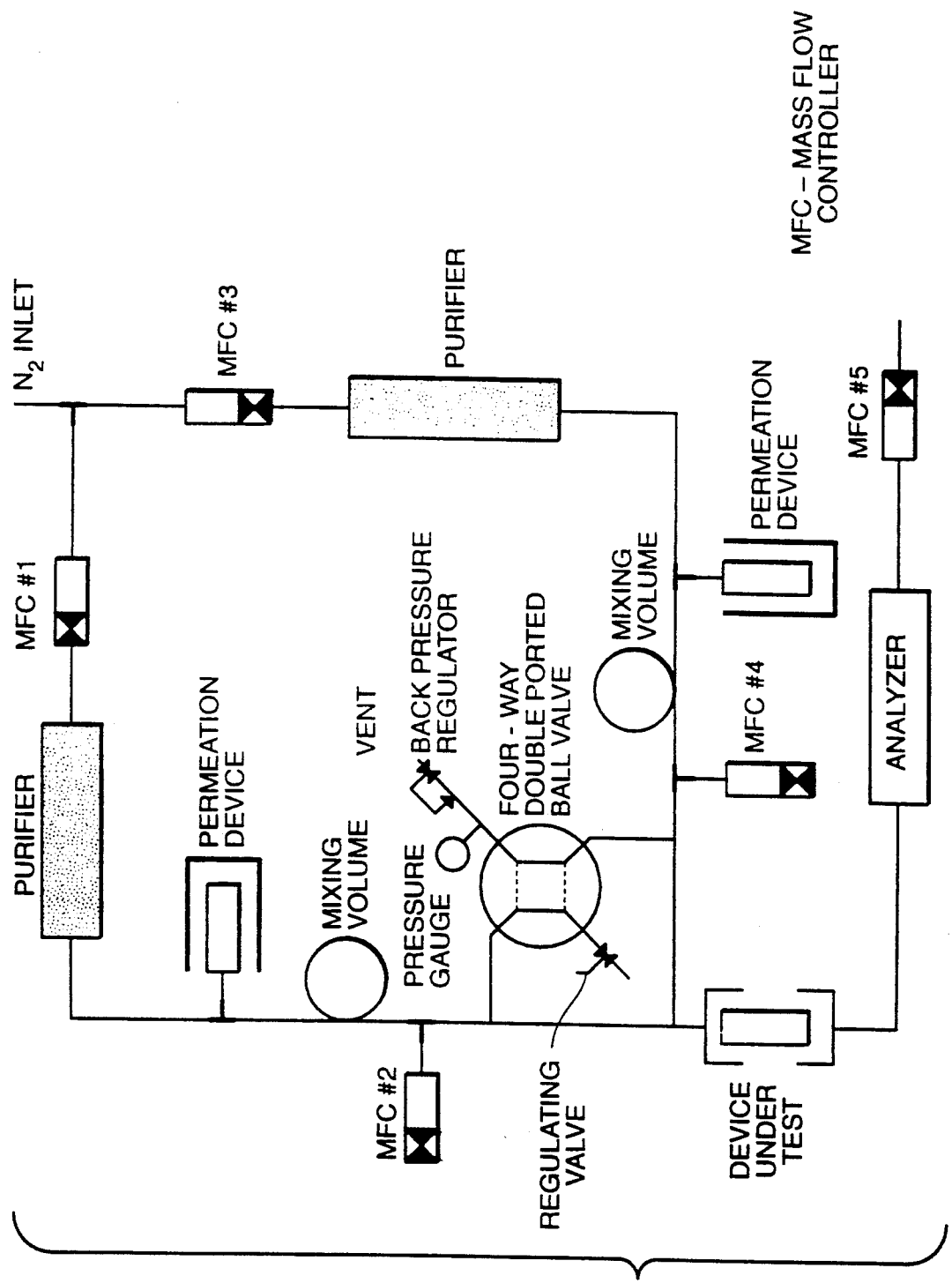
FIG._3

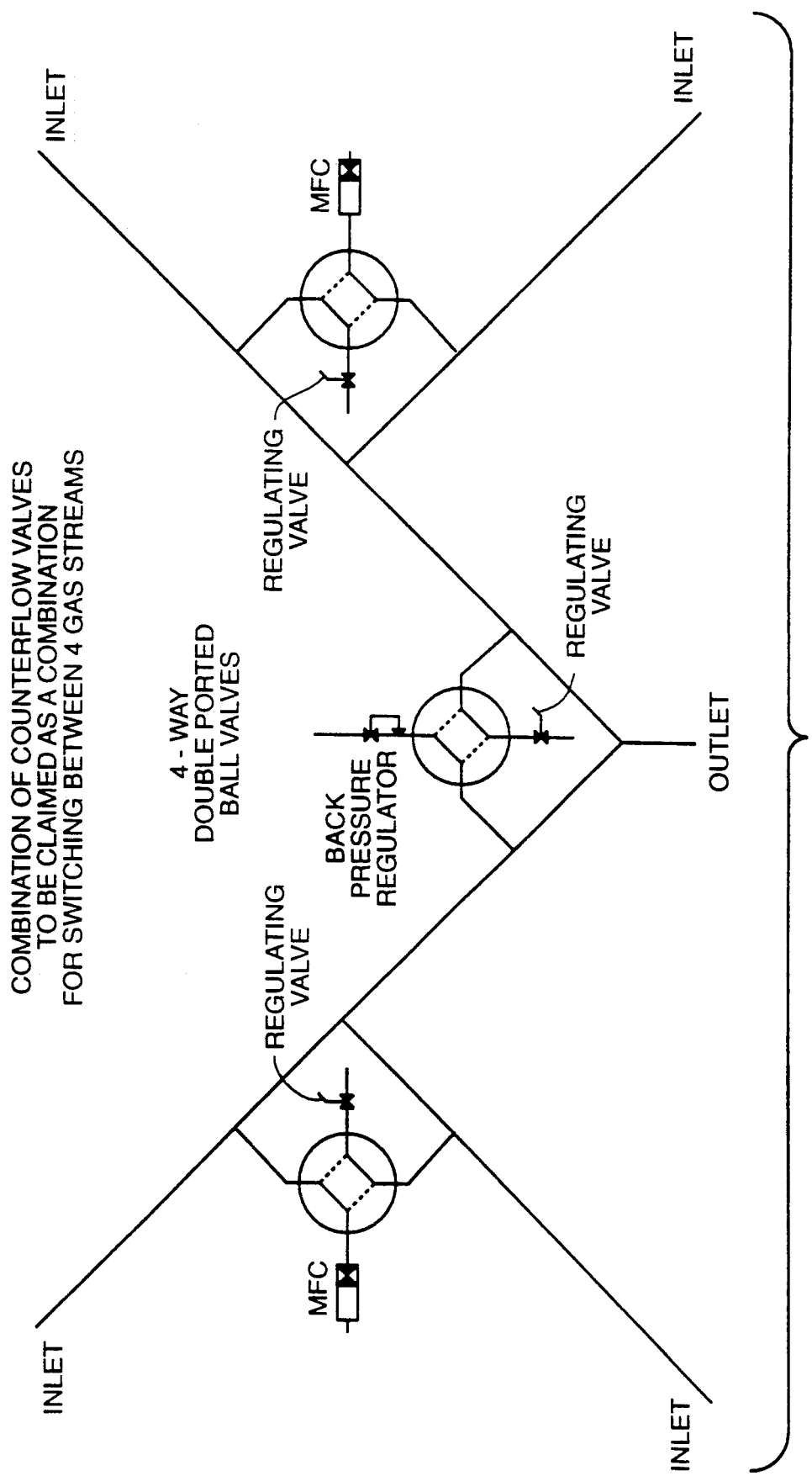
FIG._4

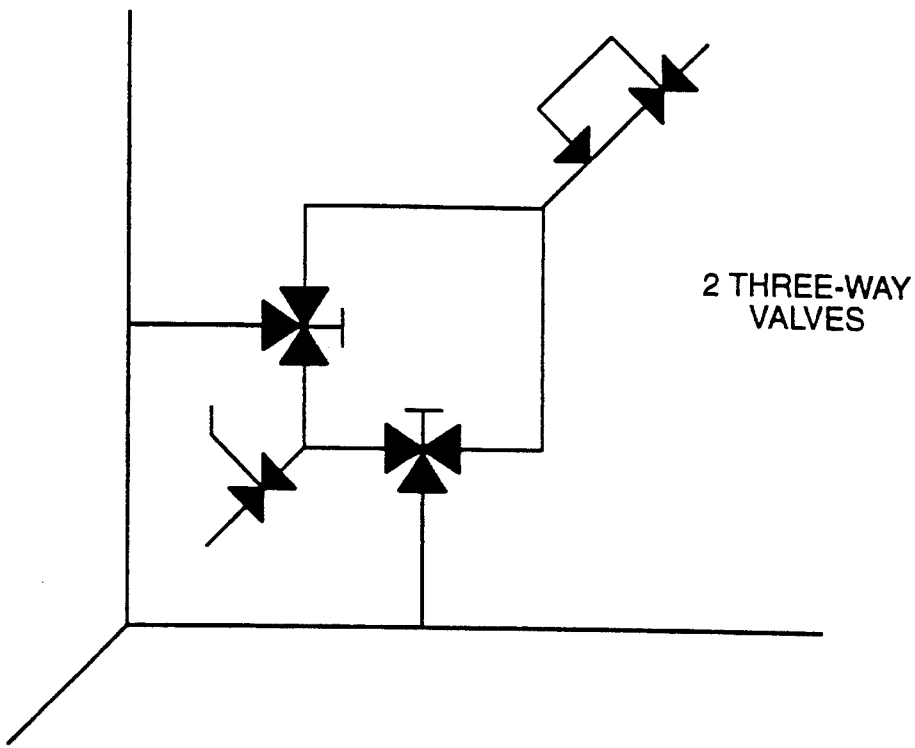
FIG._5
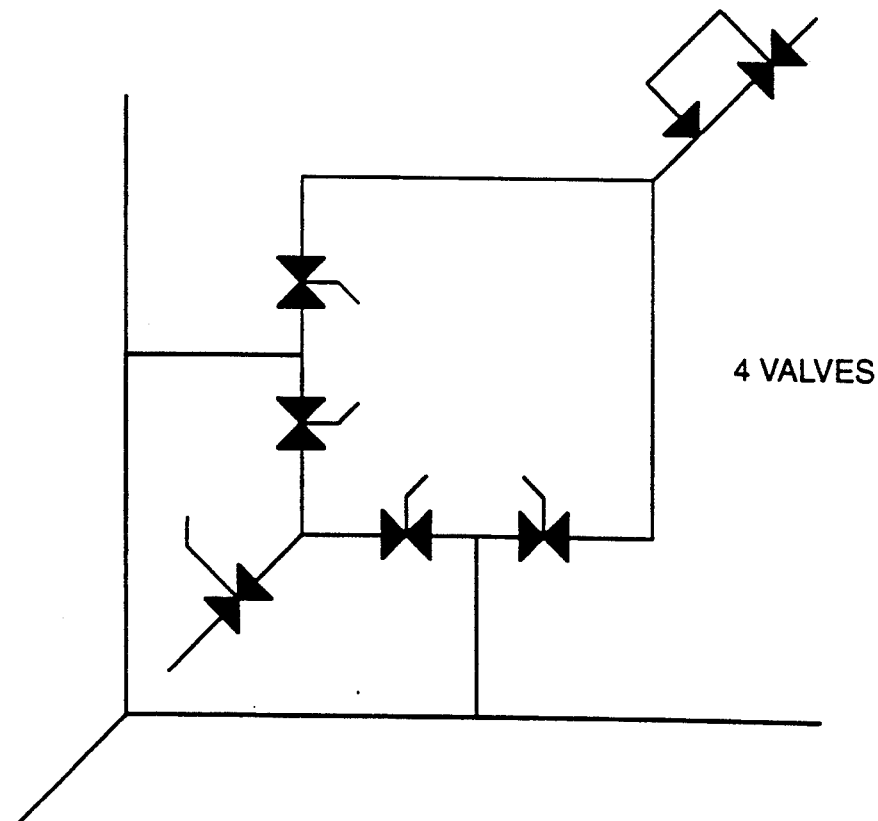
FIG._6

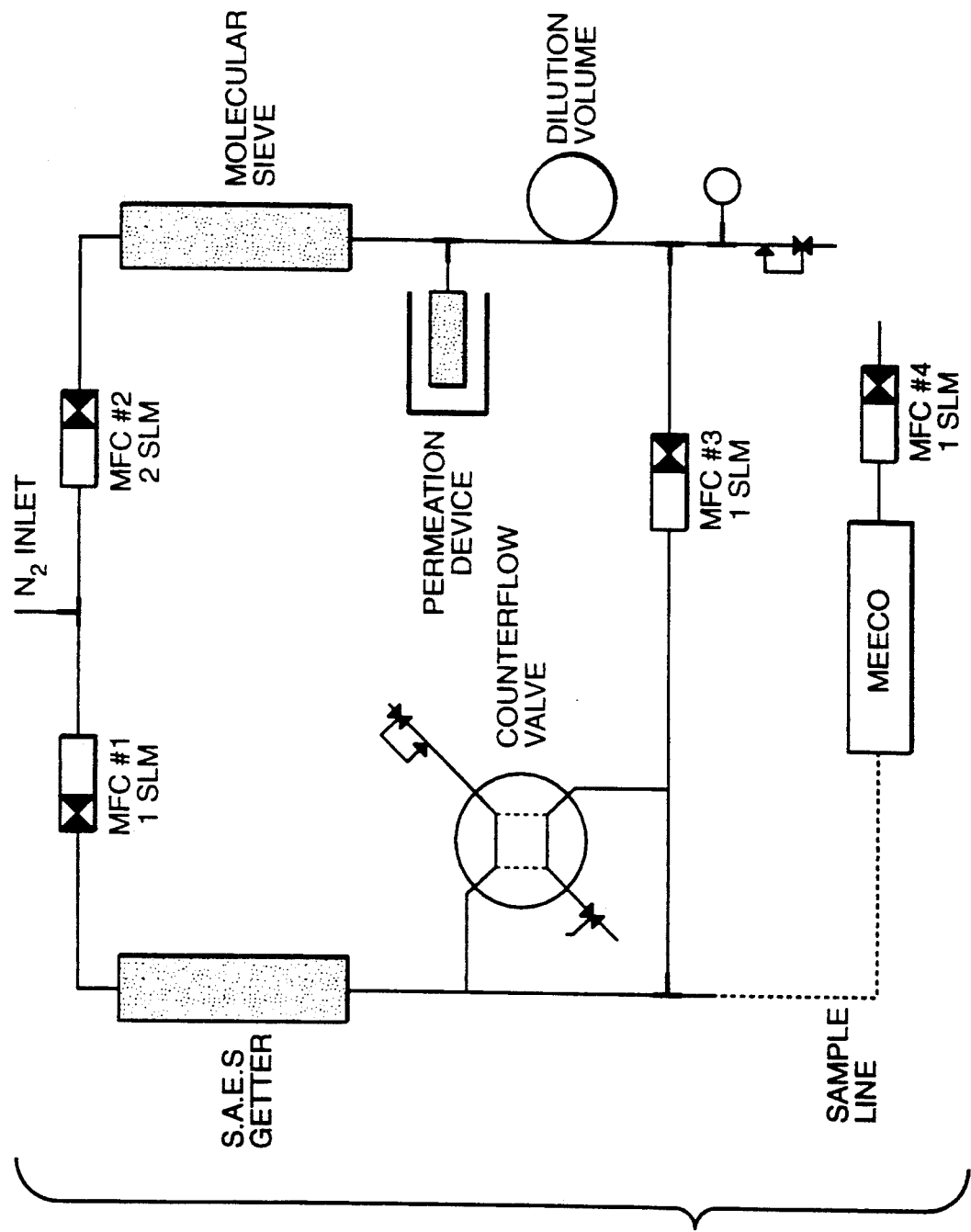
FIG._7

COUNTERFLOW VALVE

BACKGROUND OF THE INVENTION

1. Field of the Invention

The present invention relates to a valve or valving system which may be used for switching between flowing gas streams without the undesirable interaction of the gas with any dead volume area or non-metallic surfaces.

2. Description of the Background

As the demand for integrated circuits having higher densities has increased, so also has the demand for process gases of ever increasing purity. In order to obtain such gases, it is necessary to use ultra-high purity gas distribution systems. In order to more fully understand the operation of the various components of an ultra-high purity gas distribution system, however, it is necessary to ascertain the effect of impurities on the gas distribution system components.

The gas distribution system components can be tested using an apparatus which is capable of rapidly switching between a high purity gas and a gas doped with a known quantity of impurity. In such a test, comparative information is obtained regarding the relative response of the various components of the gas distribution system to a disturbance or perturbation from a high purity environment. In more detail, a pulse of impurity is injected into a particular component to ascertain what, if any, interactions occur between the particular impurity and the internal surfaces and geometries of the test device.

Where the component being tested has a far greater surface interaction than the combination of switches or valves which may alternately be used, the relatively small contribution from the alternate switching or valve system may be neglected. However, where the component has a surface interaction which is not much greater than or is of approximately the same magnitude as the combination of valves which may alternately be used, the contribution from the alternate switching or valve system cannot be neglected.

Unfortunately, at present, no means exists for adequately determining which component is most desirable for a particular application, particularly in systems where a component of interest has a surface interaction which is not much greater than or is of approximately of the same magnitude as the combination of valves which may alternately be used.

SUMMARY OF THE INVENTION

Accordingly, it is an object of the present invention to provide a counterflow valve, which is capable of rapidly equilibrating a switch between gases of differing purity without permitting the gases to interact with dead volume areas or contamination surfaces.

It is also an object of the present invention to provide a counterflow valve, containing a multi-way double ported ball valve connected to metal surfaces which introduces no contamination to gases passing through the counterflow valve, and which is advantageously used in ultra-high purity gas distribution systems.

Accordingly, the above objects and others which will become more apparent in view of the following, are provided by a counterflow valve system, containing a) four-way valve means having a first and second input and a first and second output, and containing a first position wherein the first input is connected to the first output and the second input is connected to the second output, and a second position wherein the first input is connected to the second output and the second input is connected to the first output, b) first inlet duct means, containing a first leg, and a second leg, said first leg being connected to said first input, said first inlet duct means being adapted to receive a flow of a first gas or gas mixture, c) second inlet duct means, containing a first leg and a second leg, the first leg being connected to the second input, the second inlet duct means being adapted to receive a flow of a second gas or gas mixture, d) pressure regulation means having an input connected to the first output and an output connected to a first vent gas means, e) adjustable flow control orifice means having an input connected to said second output and an output connected to a second vent gas means, and f) valve outlet duct means having an input connected to said second leg of said first inlet duct means and to said second leg of said second inlet duct means and an output for connection to a device adapted to receive a flow of a mixture of said first gas or gas mixture and said second gas or gas mixture.

BRIEF DESCRIPTIONS OF THE DRAWINGS

FIG. 1 illustrates the counterflow valve of the present invention in position "A" with stream 2 at the valve outlet.

FIG. 2 illustrates the counterflow valve of the present invention in position "B" with stream 1 at the valve outlet.

FIG. 3 illustrates a component testing apparatus, in accordance with the present invention, which incorporates therein the present counterflow valve.

FIG. 4 illustrates the use of multiple counterflow valves in accordance with the present invention, which may be used to switch between four gas streams.

FIG. 5 illustrates the combined use of two three-way valves in accordance with the present invention.

FIG. 6 illustrates the combined use of four valves in accordance with the present invention.

FIG. 7 illustrates another component testing apparatus, in accordance with the present invention, which incorporates therein the present counterflow valve.

DETAILED DESCRIPTION OF THE PREFERRED EMBODIMENTS

The present invention provides a valving system to switch between flowing gas streams without the undesirable interaction of the gas with any dead volume areas or non-metallic surfaces. In accordance with the present invention, the gas is exposed only to metal surfaces with absolutely no contamination, either particle or chemical, being introduced during the switch from on stream to the other.

The metal surfaces as described above are preferably clean electropolished metal surfaces, which are able to preclude the introduction of either particle or chemical contamination during the switch from one stream to another.

In one aspect, the present invention provides a counterflow valve, containing a multi-way double ported ball valve connected to chemically inert metal surfaces.

In another aspect, the present invention provides groupings of two or more similar counterflow valves into a multiple stream sampling system.

In essence, the present invention provides a counterflow valve system, which entails:

a) four-way valve means having a first and second input and a first and second output, and containing a first position wherein the first input is connected to the first output and the second input is connected to the second output, and a second position wherein the first input is connected to the second output and the second input is connected to the first output, b) first inlet duct means, containing a first leg, and a second leg, the first leg being connected to the first input and the first inlet duct means being adapted to receive a flow of a first gas or gas mixture, c) second inlet duct means, containing a first leg and a second leg, the first leg being connected to the second input, the second inlet duct means being adapted to receive a flow of a second gas or gas mixture, d) pressure regulation means having an input connected to said first output and an output connected to a first vent gas means, e) adjustable flow control orifice means having an input connected to the second output and an output connected to a second vent gas means, and f) valve outlet duct means having an input connected to the second leg of the first inlet duct means and to the second leg of the second inlet duct means, and an output for connection to a device adapted to receive a flow of a mixture of the first gas or gas mixture and the second gas or gas mixture.

The counterflow valve of the present invention is advantageous due to the non-contaminating nature of the valve as well as the superior equilibration time afforded by the valve for switching between gas streams.

The term "counterflow valve" is used in the present specification to mean a valve or valving system which may be used to switch between flowing gas streams without the undesirable interaction of the gas with any dead volume areas or contaminating surfaces. Such a valve or valving system is capable of rapidly equilibrating a switch between gases of differing purity. Further, although the present valve contains a ball valve, gas streams which are available at the exit of the valve system are protected against undesirable interaction with the ball valve.

The present counterflow valve may contain, for example, one double ported four-way valve or two three-way valves or four shut off valves. However, it is advantageous to utilize a four-way double ported ball valve, such as the Whitey, SS-43YF2, which is connected to electropolished stainless steel ¼" tubing and electropolished Microfit ® butt weld fittings in such a way as to create a flow pattern which is reversed as the four-way valve is switched. The outlet of the counterflow valve is exposed to this reversing flow pattern and thus the gas which is available at the outlet is determined by the position of the four-way valve. The operation of this counterflow valve may be seen from FIGS. 1 and 2. A most important requirement for the proper operation of this valve is that the flow of inlet streams 1 and 2 be controlled.

In more detail, and by reference to FIG. 1, the various flow rates for component portions of the counterflow valve and their relationships will now be discussed. Generally, it is seen that flow stream 1 is designated $x_1$ from the first inlet duct means. This constitutes a first source of gas or gas mixture. Flow stream 2 from the second inlet duct means is designated $x_2$. This constitutes a second source of gas or gas mixture.

Flow stream 1 proceeds into the first leg and then to the first input and then to the first output.

Flow stream 2 proceeds into a first and second leg. The first leg of flow stream 2 is designated $y_2$ and proceeds to a second input and then to a second output. The second leg of flow stream 2 is designated $(x_2 - y_2)$ as shown at the bottom portion of FIG. 1. The second leg of flow stream 2 proceeds, as shown, and is designated $(x_2 - y_2 - z)$. Then, flow stream 2 proceeds to the first input, as shown, and is designated $x_1 + (x_2 - y_2 - z)$. $z$ represents flow stream 2 at outlet duct means.

Also shown in FIG. 1 are a back pressure regulator in fluid connection with the first vent, an adjustable flow control orifice in fluid connection with the second vent, and the four-way valve with two positions.

In accordance with the present invention, it is preferred that the following flow conditions be used:

$$x_1 \text{ or } x_2 > z + y_2, \quad (1)$$

and $$x_1 \text{ or } x_2 = z + y_2 \, \Delta \quad (2)$$

wherein $\Delta$ is at least about 50 sccm, i.e., standard cubic centimeters per minute.

As mentioned, $\Delta$ will generally have a value of at least about 50 sccm. However, this approximate minimal value is typically used in conjunction with a ¼ inch diameter tube, but will vary depending upon the length and the diameter of tubing used. For example, with wider diameter tubes a higher value of $\Delta$ is required, such as 60, 75 or even 100 sccm.

In FIG. 1, it can be seen that flow stream 1 and flow stream 2 at 500 sccm and 150 sccm, respectively, flow from the first input to the first output, and flow stream 2 at 50 sccm proceeds from the second input to the second output. This constitutes a first position or position "A" for the counterflow value.

In FIG. 2, a second position or position "B" for the counterflow valve is illustrated. In essence, flow stream 1 at 50 sccm proceeds from the first input to the second output, and flow stream 2 at 500 sccm proceeds from the second input to the second output.

FIG. 3 illustrates the use of the present counterflow valve in a device for testing a particular component. This figure shows the use of the present counterflow valve with 5 mass flow controllers, 2 permeation devices, 2 purifiers and 2 mixing devices, in the relationship shown, for testing a device such as a component of a gas distribution system.

The switching valve of FIG. 3 is illustrated in an apparatus for delivering a step function and pulsed moisture concentrations. It generally entails two means for generating desired concentrations of a compound and a means for switching between the two-gas streams. The means for generating the desired concentration of a compound are well described in U.S. Pat. No. 4,849,174, which is incorporated herein in the entirety.

The flow of vector gas is controlled by mass flow controllers #1 and 3, i.e., MFC #1 and MFC #3, through a purifier and over a permeation device which is temperature controlled to ensure a constant rate of permeation.

The impurity-doped vector gas is vented through MFC #2 and MFC #4 while about 500 cc is preserved to feed the counterflow valve. Notably, only electropolished stainless steel is in contact with the vector gas after the purifier, except the permeation device. This arrangement is very advantageous for ultra-high purity work.

FIG. 4 illustrates the use of multiple counterflow valves for switching between 4 gas streams. Notably, as shown, 3 four-way double ported ball valves are employed as regulating valves.

However, other arrangements and combinations may be used in using the present counterflow valve.

For example, instead of using mass flow controllers, generally any flow control means may be used. However, the flow itself is variable. The important consideration is that regardless of the flow rate selected, the flow must be controlled. Mass flow controllers are advantageously used, however, as the set point for flow may be easily changed. Valves may also be used as a flow control means, but generally mass flow controllers are preferred.

Further, in FIG. 3, the analyzer used may be any form of instrumentation which is appropriate for the species being detected. For example, if moisture is to be detected, a hygrometer may be used. If oxygen is to be detected, a mass spectrometer may be used. A mass spectrometer may also be used when detecting organic compounds.

Moreover, although FIG. 3 illustrates the use of two permeation devices, one permeation device may be used alone. For example, from FIG. 3, if permeation device #2 were removed, then it is unnecessary to use the mixing volume and MFC #4. MFC #3 is still used as a control means, however.

As a detailed, and non-limitative example, if a flow of 500 cc is required, MFC #3 is set to 650 cc, substracting 150 cc from MFC #4, to avoid dead volume.

In FIG. 3, the purifier content will depend upon the inlet gas. For example, if the interaction of a gas component and water is desired, a molecular sieve may be used as a purifier. A different molecular sieve will be used, however, if the interaction of a gas component and carbon dioxide is desired. If the interaction of a gas component and oxygen is desired, a getter may be used. Such molecular sieves, getter and purifiers containing the same are well known to those skilled in the art.

As noted above, one or more permeation devices may be used. When using two or more permeation devices, each device may have the same permeate or a different permeate or use the same or a different permeation rate. Such devices are known to the artisan.

The mixing volume is a system which ensures homogeneous mixing of gas mixtures. The mixing volume may be of any shape, however, it is usually a looping system, a straight line or a sophisticated set of twisting coils. The particular shape of the mixing volume used largely depends upon the flow rate of the gas used.

In accordance with the present invention, the device tested in the testing apparatus of the present invention may be any component of an ultra-high purity gas delivery system. For example, valves, tubes or any other component may be tested. As noted above, the test may be devised to test the effect of any potential contaminant, such as moisture, oxygen, carbon dioxide, or organic compounds on the component.

Although the present invention may be practiced so as to test more than one component at a time, it is generally preferred to test only one component at a time.

Generally, in assembling the testing apparatus of the present invention, the electronic flow control means is positioned upstream of the purifier. Further, in experiments which entail a progression from zero level of pulse to an elevated level of pulse, one permeation device is generally used. In experiments which entail a progress from a first elevated level of pulse to a second elevated level of pulse, two permeation devices are generally used. Generally, however, the experimental sensitivity appears to be greater for experiments which entail a progression from zero level of pulse to an elevated level of pulse.

Returning to the figures FIG. 5 illustrates the use of two three-way valves in accordance with the present invention.

FIG. 6 illustrates the use of four valves in accordance with the present invention.

FIG. 7 illustrates a component testing apparatus, in accordance with the present invention, which incorporates therein the present counterflow valve.

In more detail, FIG. 7 illustrates the use of a back pressure regulator to regulate pressure over a permeation device. However, FIG. 7 illustrates only one apparatus configuration, and pressure may be regulated using other apparatus configurations.

The counterflow valve of the present invention generally contains a four-way double ported ball valve. However, it may instead contain two three-way valves or four shut-off valves.

The present invention also provides a process for switching between flowing gas streams without the undesirable interaction of the gas with any dead volume area or non-metallic surfaces or both, which entails:

a) passing a first gas or gas mixture from a first source to a first inlet duct means containing a first leg and a second leg, the first leg being connected to a first input, b) passing a second gas or gas mixture from a second source to a second inlet duct means containing a first leg and a second leg, the first leg being connected to a second input, c) passing the first gas or gas mixture and the second gas or gas mixture into four-way valve means having a first and second input and a first and second output and having a first position wherein the first input is connected to the first output and the second input is connected to the second output and a second position wherein the first input is connected to the second output and the second input is connected to the first output, whereby in the first position the first gas or gas mixture passes from the first input to the first output and the second gas or gas mixture passes from the second input to the second output, and in the second position the first gas or gas mixture passes from the first input to the second output and the second gas or gas mixture passes from the second input to the first output, and d) passing the first gas or gas mixture from the four-way valve means to a pressure regulation means and the second gas or gas means to an adjustable flow control orifice means when the valve means is in the first position, or passing the first gas or gas mixture to the adjustable flow control orifice means and the second gas or gas mixture to the pressure regulation means when the valve means is in the second position.

The present invention also provides an apparatus for testing the interaction of one or more low level impurities with one or more components of an ultra-high purity gas distribution system, which entails:

a) an inert or diluent gas inlet duct means fluidly connected to a first and second leg, b) the first leg containing electronic flow control means, a purifier and permeation device, in order, downstream of the inert or diluent gas inlet, and being fluidly connected to a first input of a counterflow valve means, c) the second leg containing a purifier and a permeation device, in order, downstream of the inert or diluent gas inlet, and being fluidly connected to a second input of the counterflow valve means, d) the first and second leg further being fluidly connected downstream of the counterflow valve means to means for testing said one or more components of said ultra-high purity gas distribution system, and wherein the counterflow valve means contains:

i) four-way valve means having a first and second input and a first and second output, and containing a first position wherein the first input is connected to the first output and the second output is connected to the second output, and a second position wherein the first input is connected to the second output and the second input is connected to the first output;

ii) first inlet duct means, containing a first leg, and a second leg, the first leg being connected to the first input, the first inlet duct means being adapted to receive a flow of a first gas or gas mixture, iii) second inlet duct means, containing a first leg and a second leg, the first leg being connected to the second input, the second inlet duct means being adapted to receive a flow of a second gas or gas mixture, iv) pressure regulation means having an input connected to the first output and an output connected to a first vent gas means, v) adjustable flow control orifice means having an input connected to the second output and an output connected to a second vent gas means, and vi) valve outlet duct means having an input connected to said second leg of the first inlet duct means and to the second leg of the second inlet duct means and an output for connection to a device adapted to receive a flow of a mixture of the first gas or gas mixture and the second gas or gas mixture.

Further, in the apparatus of the present invention, it is also feasible, and may be advantageous, to use two electronic flow control means, i.e., one for each purifier and upstream thereof relative to the inert or diluent gas inlet.

Additionally, a mixing volume may be used between each permeation device and the counterflow valve means.

The present invention also provides a combination of counterflow valve means as depicted in FIG. 4.

In accordance with FIG. 4, three counterflow valve means are fluidly interconnected so as to provide the capability of switching between four gas streams.

In particular, a first counterflow valve means having a first and second inert or diluent gas inlet means, and having electronic flow control means therefor is fluidly connected to a second counterflow valve means, said second counterflow valve means also having a first and second gas inlet means and having a back pressure regulator.

The second counterflow valve means is fluidly connected to a third counterflow valve means also having electronic flow control means, the third counterflow valve means having first and second gas inlet means, and wherein the first and second inlet means of the second counterflow valve means are fluidly connected to the first and third counterflow valve means outlets.

In this apparatus, it is preferred that the electronic flow control means be a mass flow controller, and that the counterflow valve means be a four-way double ported ball valve.

FIGS. 5 and 6 will now be discussed in more detail.

The apparatus of FIG. 5 contains a combination of two three-way valves in fluid connection with a valve and a back pressure regulator. Any standard valve, back pressure regulator, and three-way valves may be used. However, it is preferred if three-way ball valves are used. For example, as the three-way ball valves, the Whitey - 43XS4 may be used. More particularly, the Whitey SS-43XS4 (stainless steel) three-way ball valve may be used.

The apparatus of FIG. 6 contains a combination of four valves in fluid connected with a valve and a back pressure regulator. Any standard four shut-off valves, shut-off valve and back pressure regulator may be used.

Having described the present invention generally, reference will now be made to certain examples which are provided solely for purposes of illustration and are not intended to be limitative.

EXAMPLE 1

In order to describe the operation of the counterflow valve of the present invention, the inlet flow of streams 1 and 2 from FIGS. 1 and 2 are defined as being equal to 500 cc/min. However, it is not necessary that the flows be equal to 500 cc/min. The flow at the outlet valve is defined as being 300 cc/min. From FIGS. 1 and 2, with the four-way valve in position "A" or "B", the pressure in the counterflow valve can be regulated using the back pressure regulator since the combined inlet flow of 500+500 cc/min is greater than the flow from the outlet (300 cc/min) plus the flow from the regulating valve to vent. The pressure in the counterflow valve may be monitored at point X of FIGS. 1 and 2, if desired. This is not shown in FIGS. 1 and 2, however, as a pressure gauge is not necessary for the operation valve. With the pressure regulated at the desired level, a flow across the regulating valve can be established. Using the above figures, a flow of 50 cc/min through the regulating valve to the vent is sufficient to maintain a reverse flow in the tubing connecting the four-way valve to the counterflow region, which is adequate to protect the counterflow region from the influences of the relatively inexpensive four-way valve.

Having established the inlet and outlet flows of the valve, the flow pattern for the two positions of the four-way ball valve can be calculated. FIG. 1 describes the flow pattern in the counterflow valve when the double ported four-way valve is in position "A". The flow from inlet stream 2 (500 cc/min) is divided between two legs at the first intersection. 50 cc/min is directed toward the four-way valve and vented through the regulating valve while 450 cc/min proceeds to the next junction where it is, again, divided.

300 cc/min is required by the counterflow valve outlet leaving 150 cc/min to flow to the next junction to be opened by inlet stream 1 and forced to vent through the back pressure regulator. At the same time, the inlet flow of stream 1 is 500 cc/min and is opposed at the first intersection resulting in the entire 500 cc/min from stream 1 and the remaining 150 cc/min from stream 2 being vented through the back pressure regulator.

FIG. 2 describes the flow pattern in the counterflow valve when the double ported four-way valve is in the "B" position. The flow pattern is the exact reverse of the previous description for position "A" thus making stream 1 available at the outlet of the counterflow valve.

By maintaining a flow through the regulating valve in FIGS. 1 and 2, a gas velocity is established in the tubing between the four-way valve and the inlet stream in excess of the velocity of retrodiffusion of contamination from the four-way valve. Thus, this high purity switching system is protected from the influences of a relatively low purity, inexpensive valve. Furthermore, there are no dead volumes or contamination surfaces or particle generating surfaces in contact with the gas being sampled from the counterflow valve outlet.

In order to obtain a better understanding of the interaction of various low level impurities with various components of an ultra-high purity gas distribution system, it is advantageous to use an apparatus which is capable of switching very quickly between a high purity gas and a gas doped with a known quantity of the impurity of interest.

In such a system, a "slug" of impurity may be introduced into the components being evaluated such as valves, tubing, filters, and mass flow controllers. The magnitude and duration of the slug of impurity is controlled. The deformation and retention of the slug as it passes through the test component is recorded and is a result of the gas surface interactions between the impurity and the test component. Such a pulse generator is advantageously used to understand gas-surface interactions.

In conducting such an experiment, it is important to employ an apparatus which is capable of switching very quickly between a high purity gas and a gas doped with a known quantity of impurity. In such a system, the magnitude of the impurity pulse is controlled using known permeation technology, while the time domain of the pulse is controlled by the present counterflow valve. This technique is important in assessing the impact that a given impurity has on a particular system component.

For example, the moisture content of process gases is a critical parameter of VLSI semiconductor manufacture. Moisture interacts strongly with surfaces with which it comes into contact and can be very difficult to remove therefrom. Thus, if the moisture content of a gas is low at the supply point, its concentration level at the point of use will be largely determined by the intervening distribution system. The critical moisture range is on the order of 50 ppb, below which the components, surface treatments and pre-treatment begins to dominate the time response of systems with regard to initial dry-down or upset conditions during operation.

In fact, several examples of operational scenarios that can lead to variations of moisture levels at the output of a gas line, such as changes in inlet concentration or flow rate, may be mentioned. Such variations or "complex events" can be simulated straightforwardly by the way a system responds to an upset condition is not easily evident from the initial dry-down pattern, unless one can clearly distinguish between (i) the amount of moisture initially present, (ii) the extent to which moisture interacts with the component. This may be called the degree of "transparency" of the component.

Contributing factor (i) is determined essentially by the pre-treatment of the component, such as purging and/or baking and by its packaging. Factor (ii) depends on surface properties (finish and composition) and dead-volumes, and largely determines a system's speed of recovery from a given upset. Thus, additional tests are required to evaluate system response to upsets.

A third point to consider in addition to the rate at which moisture adsorbs or desorbs is the diluting effect of the carrier gas flow. By using a sufficiently high flow rate of gas any amount of desorbed moisture can be diluted to essentially the purge gas moisture level. This requires that an appropriate test flow rate be defined as related to operating conditions.

The response of a component system to moisture upsets can be tested by using standard input changes such as a step-up, step-down or (square wave) pulse, generated by an appropriate moisture generator.

A particularly informative dry-down test is known in which moisture levels from various point-of-use filters are compared which have all been unpacked and coupled to the test piece via a two-way valve which enables rapid switching from one to the other. For the moist gas we have used a moisture generator of our own design which is now commercially available. The dry gas is essentially the output of a purifier, for example a molecular sieve. The quality of the two-way valve largely determines the sharpest changes in moisture level which can be generated, and this, together with the response time of the moisture analyzer, will fix the smallest differences in transparency which can be resolved. We have used a valve, of our own design, with a rather short response time, and have used several moisture analyzers, including electrolytic, vibrating quartz, and APIMS. Generally, the faster the flow rate, the faster the pulse passes through the system. The flow rate and pulse length need to be carefully chosen so as to be appropriate to a given test component. Because the electrolytic hygrometer is equipped with a bypass which can be adjusted to accommodate varying excess flow, the flow rate through the cell itself is the same in all cases.

In addition to step function responses, the initial dry-down curve may be determined, simply by leaving the valve switched to the dry gas side after introducing the component to be tested until the baseline level of the purge gas is reached. Once the dry-down is complete, the input function of choice, may be introduced which can be one of three types, namely (a) a step-up, (b) a step-down, or (c) a pulse.

By a "step-up", is meant a step from equilibrium at a lower moisture concentration to equilibrium at a higher concentration. A "step-down" is the inverse of the step-up. The pulse, like the step-up, starts from equilibrium at a lower concentration, but unlike the step-up, switches back to a lower concentration input long before equilibrium at the higher concentration is reached.

The step down function resembles the dry-down test with one significant difference that the initial conditions are now well-defined. Hence, the evaluation and ranking of components becomes unambiguous and independent of the time or moisture concentration at which the components are compared. For this type of input function, a polytetrafluoroethylene filter reproducibly dries down fastest when all three are tested from identical initial levels. Notably, there is no cross-over in the step-down curves, which might be expected as all the initial conditions are the same.

An alternative, practical method for measuring the response of components or entire systems to rapid changes in input impurity concentrations is by pulses.

Moisture pulses are generated with the same equipment as shown in FIG. 3, combining a step-up and a step-down about 1 minute apart. In this case, the input concentration does not equilibrate at the high level. Thus, pulse tests are especially useful when test duration is of concern because they permit higher repetition rates.

A further advantage of the pulse test, which lasts at least one minute in practice, is that it mimics an "upset" quite precisely. Examination of results obtained to date shows that there is an "induction time" before the moisture concentration starts to rises at all, followed by a rise to a maximum and a subsequent decay. The shorter the induction time and the higher the maximum, the more transparent the test-component. In this experiment, the oxygen passivated tubing was more transparent by both of these criteria. Results obtained on other samples of electro-polished tubing tested support this trend.

Thus, the present invention provides a new approach to testing components and/or gas distribution systems for their impact on downstream gas purity. This invention is, in part, predicated upon our understanding of how systems react to changing moisture levels, and utilizes a characterization method similar to transfer function measurements in electrical systems, i.e. establishing a relationship between output and input for a given component.

In using this methodology, it is possible to distinguish between intrinsic system properties (related to materials of construction and surface finish) which are required to make unambiguous comparisons with regard to materials and equally valuable information related to the pretreatment history, such as prepurging, and care in packaging, for example, of individual components. By being able to separate the intrinsic system properties and apparent properties arising from the pretreatment history, a more complete picture is obtained about how a given component or system will affect gas purity.

A modified version of such a pulse generator may be advantageously used to facilitate a pulse from a known level to an elevated level and back again. It is noted, however, that such generators are not limited to a pulse input to a test device. Valuable information about a component may also be obtained by utilizing a "step" increase or a decrease in concentration.

The present invention also provides an ultra-high purity gas distribution system. Of paramount concern in such a system is the ability to switch between gas streams without the undesirable contact of the gas with dead volumes or the sealing materials commonly found in valves.

As noted above, FIG. 4 is an illustration of a valve system incorporating essentially three counterflow valves to switch between four gas streams. The center valve is as previously described above. The two outside valves are similar to the previously described switching system with the exception that both venting legs of the double ported four-way valve require flow control.

Although the ultra-high purity multi-stream gas switching system has been depicted using on regulating valve and one mass flow controller on each outside valve system, the mass flow controller may be replaced by other flow control means. Pressure for this group of valves is controlled by a single back pressure regulator on the center four-way valve.

Although the valve system describe accommodates four gas streams, the valve systems of the present invention are not limited to four gas streams, and additional gas streams are specifically contemplated.

Additionally, it appears desirable that such switching systems be machined out of a single block of metal so as to decrease the size of the switching system while retaining all of the desirable features mentioned above. These features include 1) no dead volume, 2) electropolished surfaces and 3) contact of the gas stream only with metal surfaces.

Generally, the present invention also provides a process for measuring the response of one or more components to changes in concentration of a contaminant, which entails subjecting the one or more components to a change in concentration of one or more contaminants from a first to a second level, and measuring the response of the one or more components to the change in concentration, wherein the change in concentration of the one or more contaminants is effected by switching between gas streams without contacting the gas streams with dead volumes or valve sealing materials.

The above method may be practiced, as noted above, either by increasing the contaminant concentration from a first to a second level in a "step up", or by decreasing the contaminant concentration from a first to a second level in a "step down".

Generally, the time duration of the step up or step down will vary with the component being tested. However, the time duration of the step up or step down will generally vary from about 0.01 sec. to 120 min., although shorter or longer times may be used.

It is more preferred, however, if the time duration of the step up or step down has a time duration of about 10 sec. to 60 min. It is even more preferred, however, if the time duration of the step up or step down has a time duration of about 20 sec. to 5 min., most preferably from about 30 sec. to about 2 min.

For example, if a filter is tested, a slug of contaminant concentration, may be introduced and be absorbed by the filter. Then, a step up or increase in contaminant concentration may be introduced for 30 min. Then, a step down may be effected to measure the filter transparency.

However, many other examples of components which may be tested in accordance with the present invention will be apparent to the artisan in view of the above. Further, in accordance with the present invention, more than one component may be tested at a time. However, it is generally preferred to measure the response of a single component to the one or more contaminant, and preferably to only a single contaminant per each test.

Having described the present invention, it will now be apparent to one of ordinary skill in the art that many changes and modifications ca be made to the embodiments described herein without departing from the spirit in the scope of the present invention.

What is claimed as new and desired to be secured by Letters Patent of the United States is:

1. A counterflow valve means for switching between flowing gas streams without undesirable interaction of the gas with any dead volume area or non-metallic surfaces or both, comprising:
   a) four-way valve means having a first and second input and a first and second output, and containing a first position wherein the first input is connected to the first output and the second input is connected to the second output, and a second position wherein the fist input is connected to the second output and the second input is connected to the first output;

b) first inlet duct means, containing a first leg, and a second leg, said first leg being connected to said first input, said first inlet duct means being adapted to receive a flow of a first gas or gas mixture, c) second inlet duct means, containing a first leg and a second leg, the first leg being connected to the second input, the second inlet duct means being adapted to receive a flow of a second gas or gas mixture, d) pressure regulation means having an input connected to the first output and an output connected to a first vent gas means, e) adjustable flow control orifice means having an input connected to said second output and an output connected to a second vent gas means, and f) valve outlet duct means having an input connected to said second leg of said first inlet duct means and to said second leg of said second inlet duct means and an output for connection to a device adapted to receive a flow of a mixture of said first gas or gas mixture and said second gas or gas mixture, wherein said four-way valve means is a four-way double ported ball valve.

2. The counterflow valve means of claim 1, which furthers comprises a first pressure regulation means in fluid connection with said first output.

3. The counterflow valve means of claim 1, which further comprises an adjustable flow control orifice means in fluid connection with said second output.

4. An apparatus for testing the interaction of one or more low level impurities with one or more components of an ultra-high purity gas distribution system, which comprises:

a) an inert or diluent gas inlet duct means fluidly connected to a first and second leg, b) said first leg containing an electronic flow control means, a purifier and permeation device, in order, downstream of said inert or diluent gas inlet, and being fluidly connected to a first input of a counterflow valve means, c) said second leg containing a purifier and a permeation device, in order, downstream of said inert or diluent gas inlet, and being fluidly connected to a second input of said counterflow valve means, d) said first and second leg further being fluidly connected downstream of said counterflow valve means to means for testing said one or more components of said ultra-high purity gas distribution system and wherein said counterflow valve means comprises:

i) four-way valve means having a first and second input and a first and second output, and containing a first position wherein the first input is connected to the first output and the second output is connected to the second output, and a second position wherein the first input is connected to the second output and the second input is connected to the first output;

ii) first inlet duct means, containing a first leg, and a second leg, said first leg being connected to said first input, said first inlet duct means being adapted to receive a flow of a first gas or gas mixture, iii) second inlet duct means, containing a first leg and a second leg, the first leg being connected to the second input, the second inlet duct means being adapted to receive a flow of a second gas or gas mixture, iv) pressure regulation means having an input connected to the first output and an output connected to a first vent gas means, v) adjustable flow control orifice means having an input connected to said second output and an output connected to a second vent gas means, and vi) valve outlet duct means having an input connected to said second leg of said first inlet duct means and to said second leg of said second inlet duct means and an output for connection to a device adapted to receive a flow of a mixture of said first gas or gas mixture and said second gas or gas mixture.

5. The apparatus of claim 4, wherein said second leg further contains electronic flow control means upstream of said purifier.

6. An apparatus for switching between four gas streams, comprising three counterflow valve means fluidly interconnected such that an outlet duct means of a first and third counterflow valve means are each fluidly connected to a first and second inlet means, respectively, of said second counterflow valve means, and wherein each of said first, second and third counterflow valve means, comprises:

a) four-way valve means having a first and second input and a first and second output, and containing a first position wherein the first input is connected to the first output and the second input is connected to the second output, and a second position wherein the first input is connected to the second output and the second input is connected to the first output;

b) first inlet duct means, containing a first leg, and a second leg, said first leg being connected to said first input, said first inlet duct means being adapted to receive a flow of a first gas or gas mixture, c) second inlet duct means, containing a first leg and a second leg, the first leg being connected to the second input, the second inlet duct means being adapted to receive a flow of a second gas or gas mixture, d) pressure regulation means having an input connected to the first output and an output connected to a first vent gas means, e) adjustable flow control orifice means having an input connected to said second output and an output connected to a second vent gas means, and f) valve outlet duct means having an input connected to said second leg of said first inlet duct means and to said second leg of said second inlet duct means and an output for connection to a device adapted to receive a flow of a mixture of said first gas or gas mixture and said second gas or gas mixture.

7. The apparatus of claim 6, wherein each of said counterflow valve means contains a four-way double ported ball valve.

* * * * *